US006833200B2

(12) United States Patent
Senoo et al.

(10) Patent No.: US 6,833,200 B2
(45) Date of Patent: Dec. 21, 2004

(54) LUMINESCENT DEVICE WITH A TRIARYLAMINE COMPOUND

(75) Inventors: Akihiro Senoo, Kanagawa (JP); Yuichi Hashimoto, Tokyo (JP); Kazunori Ueno, Kanagawa (JP); Seiji Mashimo, Kanagawa (JP); Shinichi Urakawa, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 100 days.

(21) Appl. No.: 10/348,990

(22) Filed: Jan. 23, 2003

(65) Prior Publication Data

US 2003/0207153 A1 Nov. 6, 2003

Related U.S. Application Data

(63) Continuation-in-part of application No. 09/299,632, filed on Apr. 27, 1999, now abandoned.

(30) Foreign Application Priority Data

Apr. 28, 1998 (JP) .......................................... 10-132636

(51) Int. Cl.[7] ................................................ H05B 33/14

(52) U.S. Cl. ........................ 428/690; 428/917; 313/504

(58) Field of Search ................................ 428/690, 691, 428/704, 917; 313/504, 506; 430/59, 72, 73; 564/307, 308, 309, 426, 429, 431, 434

(56) References Cited

U.S. PATENT DOCUMENTS

| | | | | |
|---|---|---|---|---|
| 3,172,862 | A | 3/1965 | Gurnee et al. | 252/301.3 |
| 3,173,050 | A | 3/1965 | Gurnee | 313/108 |
| 3,710,167 | A | 1/1973 | Dresner et al. | 313/108 A |
| 4,356,429 | A | 10/1982 | Tang | 313/503 |
| 4,539,507 | A | 9/1985 | VanSlyke et al. | 313/504 |
| 4,720,432 | A | 1/1988 | VanSlyke et al. | 428/457 |
| 4,853,308 | A | 8/1989 | Ong et al. | 430/59 |
| 4,963,196 | A | 10/1990 | Hashimoto | 136/257 |
| 5,011,969 | A | 4/1991 | Akasaki et al. | 558/402 |
| 5,061,569 | A | 10/1991 | VanSlyke et al. | 428/457 |
| 5,344,501 | A | 9/1994 | Hashimoto et al. | 136/259 |
| 5,415,962 | A | 5/1995 | Kanemaru et al. | 430/59 |
| 5,631,404 | A | 5/1997 | Anzai et al. | 564/308 |
| 5,759,444 | A | 6/1998 | Enokida et al. | 252/301.16 |
| 6,150,043 | A | 11/2000 | Thompson et al. | 428/690 |
| 6,387,544 | B1 | 5/2002 | Thompson et al. | 428/690 |
| 2002/0048688 | A1 | 4/2002 | Fukuoka et al. | 428/690 |

FOREIGN PATENT DOCUMENTS

| | | |
|---|---|---|
| EP | 0 879 868 A2 | 11/1998 |
| JP | 59-194393 | 11/1984 |
| JP | 63-264692 | 11/1988 |
| JP | 3-163188 | 7/1991 |
| JP | 5-25473 | 2/1993 |
| JP | 7-53950 | 2/1995 |
| JP | 9-268284 | 10/1997 |
| JP | 10-95972 | 4/1998 |

OTHER PUBLICATIONS

Chemical Abstracts, vol. 128, No. 26, Jun. 29, 1998 (Abstract No. 328604).

Partridge, R.H., "Electroluminescence from polyvinylcarbazole films: 3. Electroluminescent devices", Polymer, vol. 24, No. 6, Jun. 1983, pp. 748–754.

Ogawa, T., Wakemoto, H., and Takezawa, H., "Degradation of Sub–Threshold Characteristics in a–Si TFT with Polyimide Passivation", Extended Abstracts of the 22$^{nd}$ Conference on Solid State Devices and Materials, Aug. 22–24, 1990, pp. 1039–1042.

Chen, L.J. Mayer, J.W., Tu, K.N., and Sheng, T.T., "Lattice Imaging of Silicide–Silicon Interfaces", Thin Solid Films, International Journal on the Science and Technology of Thin and Thick Films, vol. 93, No. ½, Jul. 9, 1982, pp. 91–97.

Tang, C.W. and S.A. VanSlyke, "Organic electroluminscent diodes", Appl. Phys. Lett. 51 (12), Sep. 21, 1987, pp. 913–915.

Kalinowski, J. et al., "Magnetic Field Effects on Recombination Radiation in Tetracene Crystal", Chemical Physics Letter, vol. 36, No. 3, Nov. 15, 1975, pp. 345–348.

Schwob, H.P. and Williams, D.F., "Charge transfer exciton fission in anthracene crystals", Th Journal of Chemical Physics, vol. 58, No. 4, Feb. 15, 1973, pp. 1542–1547.

Helfrich, W. et al., "Transients of Volume–Controlled Current and of Recombination Radiation in Anthracene", The Journal of Chemical Physics, vol. 44, No. 8, Apr. 15, 1966, pp. 2902–2909.

Helfrich, W. and Schneider, W.G., "Recombination Radiation in Anthracene Crystals", Physical Review Letters, vol. 14, No. 7, Feb. 15, 1965, pp. 229–231.

Pope, M., Kallmann, H.P., and Magnante, P., "Electroluminescence in Organic Crystals", Journal of Chemical Physics, Letters to the Editor, vol. 38, 1963, pp. 2042–2043, no month.

Adachi, C., Tokito, S., Tsutsui, T. and Saito, S., "Electroluminescence in Organic Films with Three–Layer Structure", Japanese Journal of Applied Physics, vol. 27, No. 2, Feb., 1988, pp. L269–L271.

(List continued on next page.)

*Primary Examiner*—Marie Yamnitzky
(74) *Attorney, Agent, or Firm*—Fitzpatrick, Cella, Harper & Scinto

(57) ABSTRACT

A luminescent device having a pair of electrodes and a luminescent layer disposed between the electrodes. The luminescent layer comprises a compound represented by the following general formula:

(1)

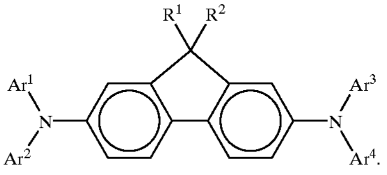

3 Claims, 3 Drawing Sheets

OTHER PUBLICATIONS

Adachi, C. Tokito, S., Tsutsui, T., and Saito, S., "Organic Electroluminescent Device with a Three–Layer Structure", Japanese Journal of Applied Physics, vol. 27, No. 4, Apr. 1988, pp. L713–L715.

Hayashi, S., Etoh, H. and Saito, S, "Electroluminescence of Perylene Films with a Conducting Polymer as an Anode", Japanese Journal of Applied Physics, vol. 25, No. 9, Sep. 1986, pp. L773–L775.

Moon, B.M., et al, "High–density Bi–Pb–Sr–Ca–Cu–O superconductor prepared by rapid thermal melt processing", Appl. Phys. Lett., vol. 55, No. 14, Oct. 2, 1989, pp. 1466–1468.

LUMINESCENT DEVICE WITH A TRIARYLAMINE COMPOUND

This application is a continuation-in-part of application Ser. No. 09/299,632, filed on Apr. 27, 1999, now abandoned, which is incorporated by reference herein.

BACKGROUND OF THE INVENTION

1. Field of the Invention

The present invention relates to a novel triarylamine compound and to a charge-injection-type luminescent device using the same. In particular, the present invention relates to a triarylamine compound applicable to a charge-injection-type luminescent device which directly converts injected charges into optical energy by an applied electric field, and relates to a luminescent device using the same.

2. Description of the Related Art

Pope et al., first discovered electroluminescence (EL) in an organic material, that is, single-crystal anthracene in 1963 (*J. Chem. Phys.*, 38, 2042 (1963)). Subsequently, Helfinch and Schneider observed relatively strong EL in an injection EL material containing a solution system having a high injection efficiency in 1965 (*Phys. Rev. Lett.*, 14, 229 (1965)).

Many studies of organic luminescent materials containing conjugated organic hosts and conjugated organic activators having condensed benzene rings have been disclosed in U.S. Pat. Nos. 3,172,862, 3,173,050, and 3,710,167; *J. Chem. Phys.*, 44, 2902 (1966); *J. Chem. Phys.*, 58, 1542 (1973); and *Chem. Phys. Lett.*, 36, 345 (1975). Examples of disclosed organic hosts include naphthalene, anthracene, phenanthrene, tetracene, pyrene, benzpyrene, chrysene, picene, carbazole, fluorene, biphenyl, terphenyl, triphenylene oxide, dihalobiphenyl, trans-stilbene, and 1,4-diphenylbutadiene. Examples of disclosed activators include anthracene, tetracene and pentacene. Since these organic luminescent materials are provided as single layers having a thickness of more than 1 μm, a high electric field is required for luminescence. Under these circumstances, thin film devices formed by a vacuum deposition process have been proposed (for example, "Thin Solid Films" p. 94 (1982); *Polymer*, 24, 748 (1983); and *J. Appl. Phys.*, 25, L773 (1986)). Although the thin film devices are effective for reducing the driving voltage, their luminance is far from levels for practical use.

In recent years, Tang, et al., have developed an EL device having a high luminance at a low driving voltage (*Appl. Phys. Lett.*, 51, 913 (1987) and U.S. Pat. No. 4,356,429). The EL device is fabricated by depositing two significantly thin layers, that is, a charge transport layer and a luminescent layer, between the anode and the cathode by a vacuum deposition process. Such layered organic EL devices are disclosed in, for example, Japanese Patent Application Laid-Open Nos. 59-194393, 59-194393, 63-264692, and 3-163188, U.S. Pat. Nos. 4,539,507 and 4,720,432, and *Appl. Phys. Lett.*, 55, 1467 (1989).

Also, an EL device of a triple-layered structure having independently a carrier transport function and a luminescent ability was disclosed in *Jpn. J. Apply. Phys.*, 27, L269 and L713 (1988). Since the carrier transportability is improved in such an EL device, the versatility of possible dyes in the luminescent layer is considerably increased. Further, the device configuration suggests feasibility of improved luminescence by effectively trapping holes and electrons (or excimers) in the central luminescent layer.

Layered organic EL devices are generally formed by vacuum deposition processes. EL devices having considerable luminance are also formed by casting processes (as described in, for example, Extended Abstracts (The 50th Autumn Meeting (1989), p. 1006 and The 51st Autumn Meeting (1990), p. 1041; The Japan Society of Applied Physics). Considerably high luminance is also achieved by a single-layered mixture-type EL device, in which the layer is formed by immersion-coating a solution containing polyvinyl carbazole as a hole transport compound, an oxadiazole derivative as an electron transport compound and coumarin-6 as a luminescent material, as described in Extended Abstracts of the 38th Spring Meeting 1991, p. 1086; The Japan Society of Applied Physics and Related Societies.

As described above, the organic EL devices have been significantly improved and have suggested the feasibility of a wide variety of applications; however, these EL devices have some problems in practical use, for example, insufficient luminance, changes in luminance during prolonged use, and deterioration by atmospheric gas containing oxygen and humidity. Further, the EL devices do not sufficiently satisfy needs for diverse wavelengths of luminescent light for precisely determining luminescent hues of blue, green and red colors in full-color displays, etc.

SUMMARY OF THE INVENTION

It is an object of the present invention to provide an organic compound applicable to a luminescent device having an optical output with significantly high efficiency and luminance.

It is another object of the present invention to provide an organic compound applicable to a luminescent device, which has diverse luminescent wavelengths, a variety of luminescent hues, and significantly high durability.

It is a further object of the present invention to provide a luminescent device easily produced at relatively low production cost and is highly safe.

An aspect of the present invention is a triarylamine compound represented by the following general formula [1]:

[1]

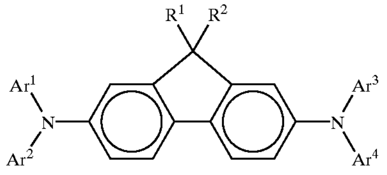

wherein $R^1$ and $R^2$ are each independently a hydrogen atom, a halogen atom, a substituted or unsubstituted alkyl group, a substituted or unsubstituted alkoxy group, or a substituted or unsubstituted aryl group; $Ar^1$, $Ar^2$, $Ar^3$, and $Ar^4$ are each a substituted or unsubstituted aryl or heterocyclic group, which may be the same or different from each other; and at least one of $Ar^1$, $Ar^2$, $Ar^3$, and $Ar^4$ is a fused aromatic ring.

Another aspect of the present invention is a triarylamine compound represented by the following general formula [2]:

[2]

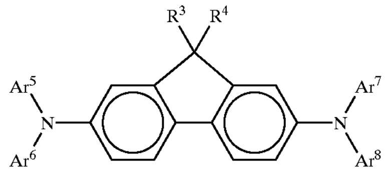

wherein $R^3$ and $R^4$ are each independently a hydrogen atom, a halogen atom, a substituted or unsubstituted alkyl group, a substituted or unsubstituted alkoxy group, or a substituted or unsubstituted aryl group; $Ar^5$, $Ar^6$, $Ar^7$, and $Ar^8$ are each a substituted or unsubstituted aryl or heterocyclic group, which may be the same or different from each other; and at least one of $Ar^5$, $Ar^6$, $Ar^7$, and $Ar^8$ is a π-conjugated aromatic hydrocarbon having 12 or more carbon atoms.

A further aspect of the present invention is a luminescent device comprising a pair of electrodes, and at least one compound among the compounds represented by the general formulae [1] or [2] disposed therebetween.

The organic luminescent device in accordance with the present invention is a thin lightweight solid device having a large area and high resolution and capable of high-speed operation, unlike conventional incandescent lamps, fluorescent lamps, and inorganic luminescent diodes, and thus satisfies advanced requirements.

DESCRIPTION OF THE PREFERRED EMBODIMENT

Figure 1:
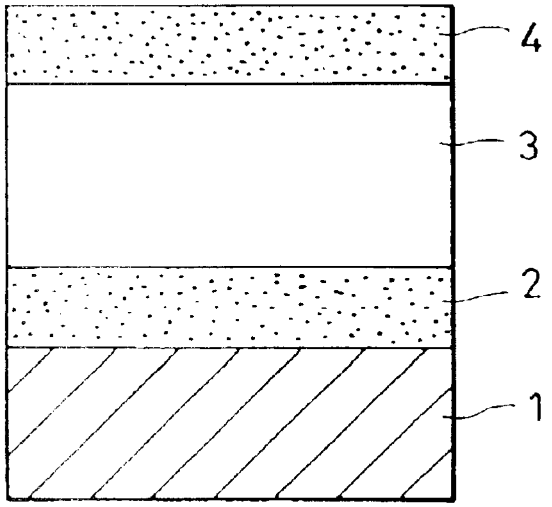
FIG. 1 is a cross-sectional view of an embodiment of a luminescent device in accordance with the present invention.

The present invention is characterized by a novel triarylamine compound represented by the general formula [1] or [2]:

[1]

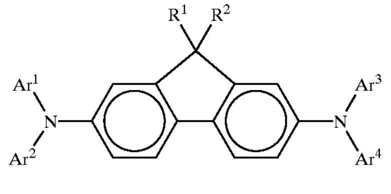

In the general formula [1], $R^1$ and $R^2$ are each independently a hydrogen atom, a halogen atom, a substituted or unsubstituted alkyl group, a substituted or unsubstituted alkoxy group, or a substituted or unsubstituted aryl group. Examples of alkyl groups include methyl, ethyl, n-propyl, and isopropyl groups; examples of alkoxy groups include methoxy, ethoxy, and phenoxy groups; and examples of aryl groups include phenyl, biphenyl, and naphthyl groups.

Examples of the substituent groups include halogen atoms, e.g., fluorine, chlorine, bromine, and iodine; alkyl groups, e.g., methyl, ethyl, n-propyl, and iso-propyl groups; alkoxy groups, e.g., methoxy, ethoxy, and phenoxy groups; aralkyl groups, e.g., benzyl, phenetyl, and propylphenyl group; a nitro group; a cyano group; substituted amino groups, e.g., dimethyl amino, dibenzylamino, diphenylamino, and morpholino groups; aryl groups, e.g., phenyl, tolyl, biphenyl, naphthyl, anthryl, and pyrenyl groups; and heterocyclic groups, e.g., pyridyl, thienyl, furyl, quinolyl, and carbazolyl groups.

In the general formula [1], $Ar^1$, $Ar^2$, $Ar^3$, and $Ar^4$ are each a substituted or unsubstituted aryl or heterocyclic group, which may be the same or different from each other. Examples of the substituted or unsubstituted aryl groups include phenyl, biphenyl, terphenyl, naphthyl, anthryl, and fluorenyl. Examples of the substituted or unsubstituted heterocyclic groups include pyridyl, furyl, thienyl, and carbazolyl groups.

At least one of $Ar^1$, $Ar^2$, $Ar^3$, and $Ar^4$ is a fused aromatic ring. Examples of the fused aromatic rings include naphthyl, anthryl, acenaphthyl, phenanthryl, naphthanyl, and fluoranthenyl rings. These fused aromatic rings may have substituent groups. Examples of the substituent groups include halogen atoms, e.g., fluorine, chlorine, bromine, and iodine; alkyl groups, e.g. methyl, ethyl, n-propyl, and iso-propyl groups; alkoxy groups, e.g., methoxy, ethoxy, and phenoxy groups; aralkyl groups, e.g., benzyl, phenetyl, and propylphenyl group; a nitro group; a cyano group; substituted amino groups, e.g., dimethyl amino, dibenzylamino, diphenylamino, and morpholino groups; aryl groups, e.g., phenyl, tolyl, biphenyl, naphthyl, anthryl, and pyrenyl groups; and heterocyclic groups, e.g., pyridyl, thienyl, furyl, quinolyl, and carbazolyl groups.

[2]

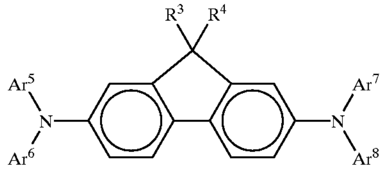

In the general formula [2], $R^3$ and $R^4$ are the same as $R^1$ and $R^2$, respectively, in the general formula [1], and $Ar^5$, $Ar^6$, $Ar^7$, and $Ar^8$ are the same as $Ar^1$, $Ar^2$, $Ar^3$, and $Ar^4$, respectively, in the general formula [1]. At least one of $Ar^5$, $Ar^6$, $Ar^7$, and $Ar^8$ is a π-conjugated aromatic hydrocarbon having 12 or more carbon atoms. Examples of the π-conjugated aromatic hydrocarbon having 12 or more carbon atoms include polyphenyls, i.e., biphenyl, p-terphenyl, and quaterphenyl; and stilbene derivatives, i.e., styryl and phenylstyryl.

The following are typical non-limiting examples of the compounds represented by the general formula [1] or [2].
Compounds represented by the general formula [1]
| Compound No. | $R^1$ | $R^2$ | $Ar^1$ / $Ar^3$ | $Ar^2$ / $Ar^4$ |
|---|---|---|---|---|
| 1 | —H | —H | 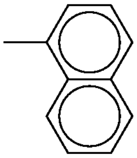 | 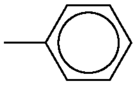 |
| | | | 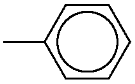 | 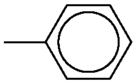 |
| 2 | —H | —H | 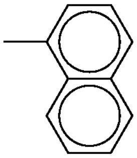 | 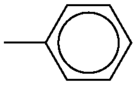 |
| | | | 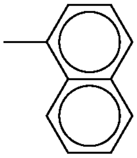 | 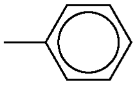 |
| 3 | —H | —H | 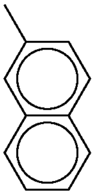 | 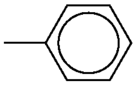 |
| | | | 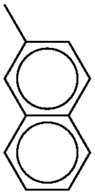 | 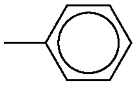 |
| 4 | —H | —H | 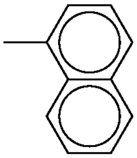 | 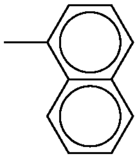 |
| | | | 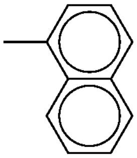 | 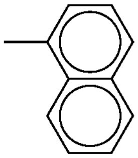 |

-continued
| Compound No. | $R^1$ | $R^2$ | $Ar^1$ / $Ar^3$ | $Ar^2$ / $Ar^4$ |
|---|---|---|---|---|
| 5 | —H | —H | 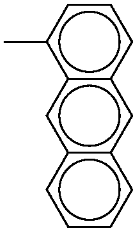 | 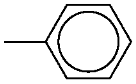 |
| | | | 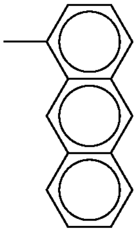 | 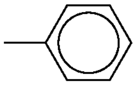 |
| 6 | —H | —H | 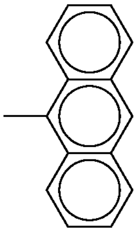 | 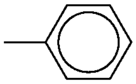 |
| | | | 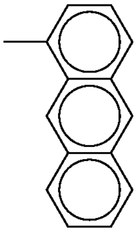 | 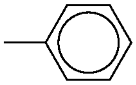 |
| 7 | —H | —H | 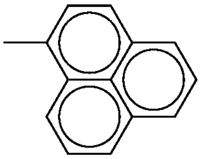 | 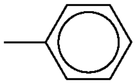 |
| | | | 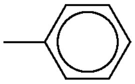 | 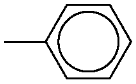 |
| 8 | —H | $-CH_3$ | 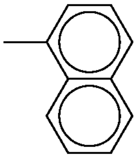 | 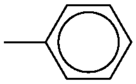 |

-continued
| Compound No. | $R^1$ | $R^2$ | $Ar^1$<br>$Ar^3$ | $Ar^2$<br>$Ar^4$ |
|---|---|---|---|---|
| | | | 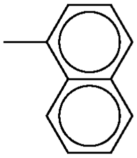 | 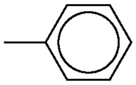 |
| 9 | —H | 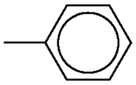 | 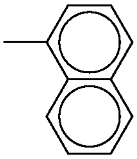 | 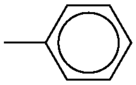 |
| | | | 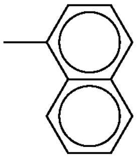 | 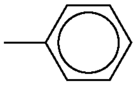 |
| 10 | —H | —Br | 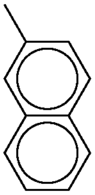 | 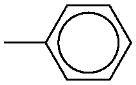 |
| | | | 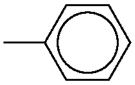 | 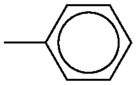 |
| 11 | $—CH_3$ | $—CH_3$ | 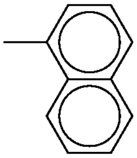 | 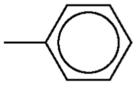 |
| | | | 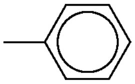 | 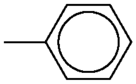 |
| 12 | $—CH_3$ | $—CH_3$ | 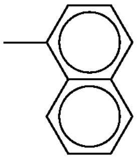 | 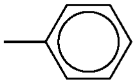 |
| | | | 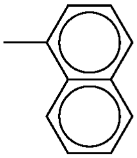 | 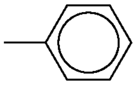 |

-continued
| Compound No. | $R^1$ | $R^2$ | $Ar^1$ / $Ar^3$ | $Ar^2$ / $Ar^4$ |
|---|---|---|---|---|
| 13 | —$CH_3$ | —$CH_3$ | 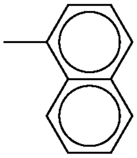 | 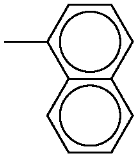 |
| | | | 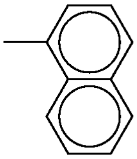 | 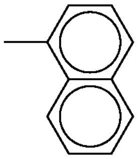 |
| 14 | —$CH_3$ | —$CH_3$ | 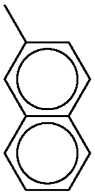 | 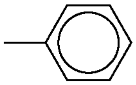 |
| | | | 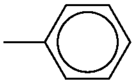 | 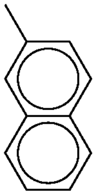 |
| 15 | —$CH_3$ | —$CH_3$ | 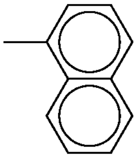 | 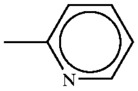 |
| | | | 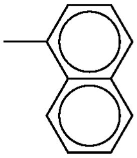 | 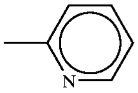 |
| 16 | —$CH_3$ | —$CH_3$ | 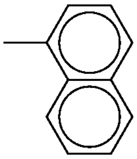 | 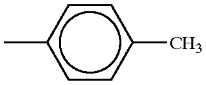 |
| | | | 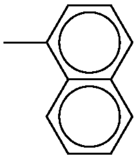 | 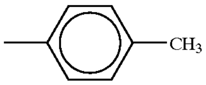 |

-continued
| Compound No. | $R^1$ | $R^2$ | $Ar^1$ / $Ar^3$ | $Ar^2$ / $Ar^4$ |
|---|---|---|---|---|
| 17 | $-CH_3$ | $-CH_3$ | 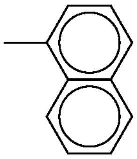 | 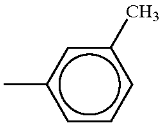 |
| | | | 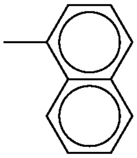 | 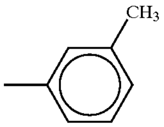 |
| 18 | $-CH_3$ | $-CH_3$ | 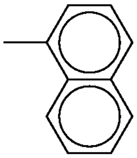 | 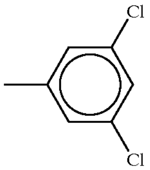 |
| | | | 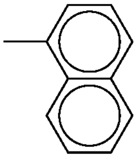 | 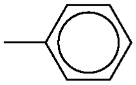 |
| 19 | $-CH_3$ | $-CH_3$ | 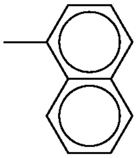 | 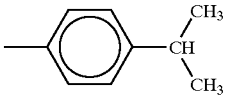 |
| | | | 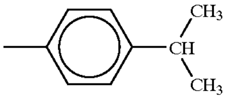 | 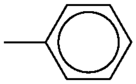 |
| 20 | $-CH_3$ | $-CH_3$ | 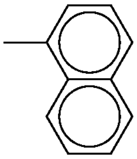 | 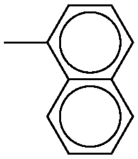 |
| | | | 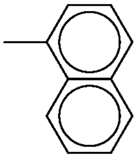 | 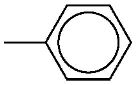 |
| 21 | $-CH_3$ | $-CH_3$ | 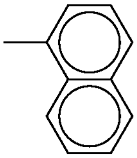 | 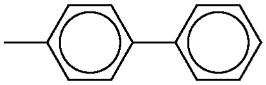 |

-continued
| Compound No. | $R^1$ | $R^2$ | $Ar^1$<br>$Ar^3$ | $Ar^2$<br>$Ar^4$ |
|---|---|---|---|---|
| | | | 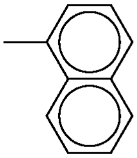 | 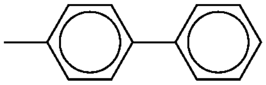 |
| 22 | $-CH_3$ | $-CH_3$ | 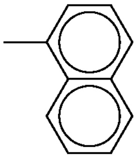 | 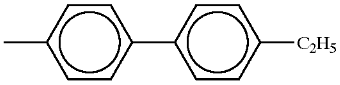 |
| | | | 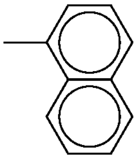 | 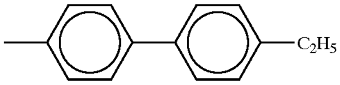 |
| 23 | $-CH_3$ | $-CH_3$ | 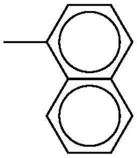 | 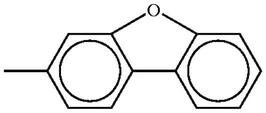 |
| | | | 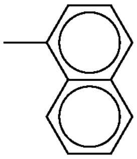 | 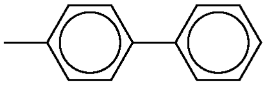 |
| 24 | $-CH_3$ | $-CH_3$ | 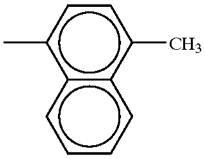 | 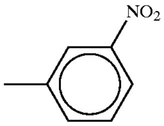 |
| | | | 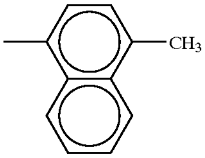 | 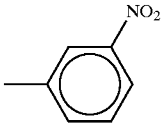 |
| 25 | $-CH_3$ | $-CH_3$ | 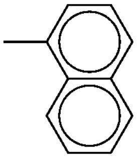 | 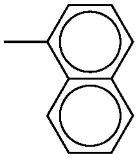 |
| | | | 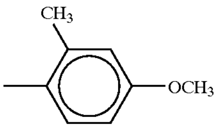 | 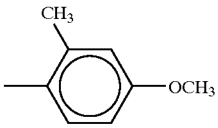 |

-continued
| Compound No. | $R^1$ | $R^2$ | $Ar^1$ $Ar^3$ | $Ar^2$ $Ar^4$ |
| --- | --- | --- | --- | --- |
| 26 | $—CH_3$ | $—CH_3$ | 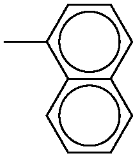 | 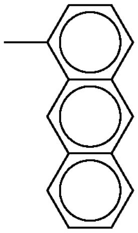 |
| | | | 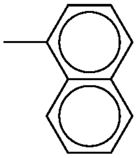 | 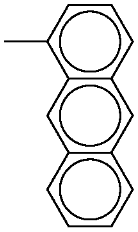 |
| 27 | $—CH_3$ | $—CH_3$ | 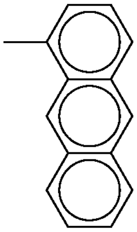 | 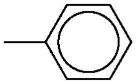 |
| | | | 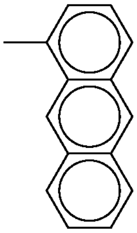 | 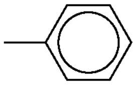 |
| 28 | $—CH_3$ | $—CH_3$ | 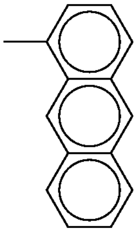 | 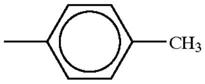 |
| | | | 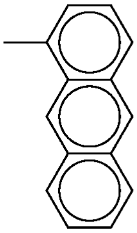 | 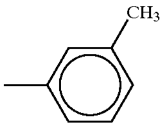 |

-continued
| Compound No. | $R^1$ | $R^2$ | $Ar^1$ / $Ar^3$ | $Ar^2$ / $Ar^4$ |
|---|---|---|---|---|
| 29 | $-CH_3$ | $-CH_3$ | 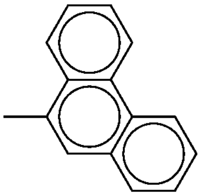 | 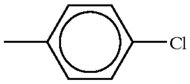 |
| | | | 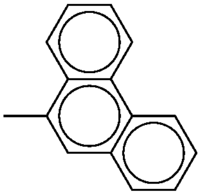 | 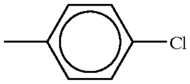 |
| 30 | $-CH_3$ | $-CH_3$ | 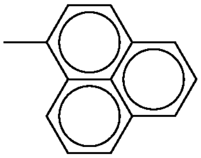 | 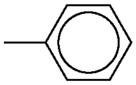 |
| | | | 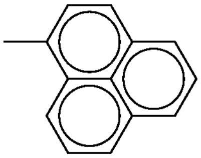 | 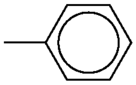 |
| 31 | $-C_2H_5$ | $-C_2H_5$ | 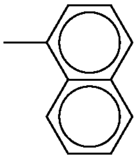 | 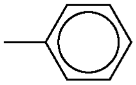 |
| | | | 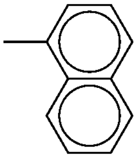 | 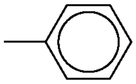 |
| 32 | $-C_2H_5$ | $-C_2H_5$ | 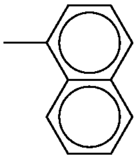 | 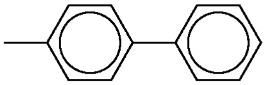 |
| | | | 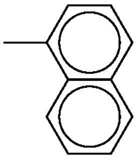 | 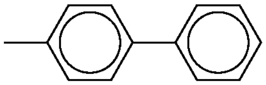 |

-continued
| Compound No. | $R^1$ | $R^2$ | $Ar^1$ $Ar^3$ | $Ar^2$ $Ar^4$ |
|---|---|---|---|---|
| 33 | $-C_2H_5$ | $-C_2H_5$ | 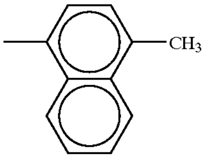 | 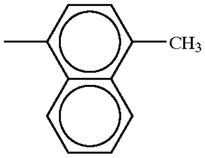 |
| | | | 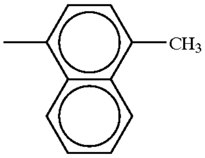 | 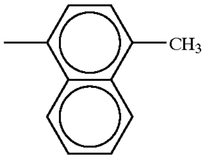 |
| 34 | $-C_2H_5$ | $-C_2H_5$ | 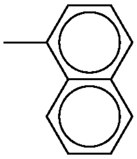 | 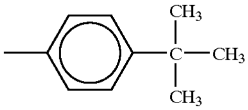 |
| | | | 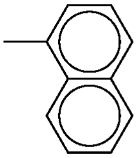 | 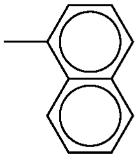 |
| 35 | $-C_2H_5$ | $-C_2H_5$ | 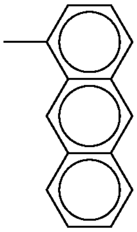 | 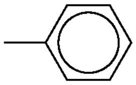 |
| | | | 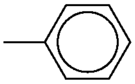 | 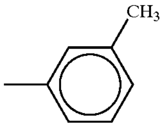 |
| 36 | $-C_3H_7$ | $-C_3H_7$ | 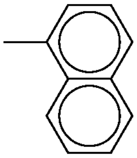 | 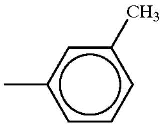 |
| | | | 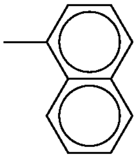 | 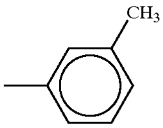 |

-continued
| Compound No. | $R^1$ | $R^2$ | $Ar^1$ $Ar^3$ | $Ar^2$ $Ar^4$ |
|---|---|---|---|---|
| 37 | $—C_3H_7$ | $—CH_3$ | 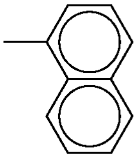 | 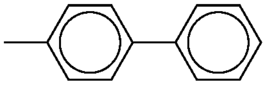 |
| | | | 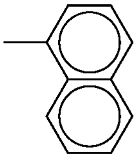 | 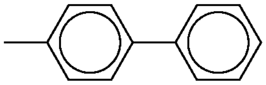 |
| 38 | $—C_3H_7$ | 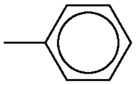 | 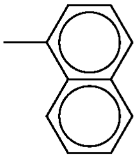 | 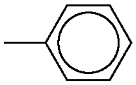 |
| | | | 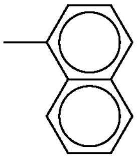 | 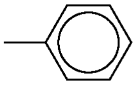 |
| 39 | $—C_4H_9$ | $—C_4H_9$ | 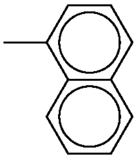 | 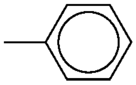 |
| | | | 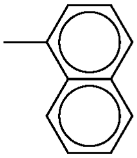 | 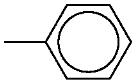 |
| 40 | $—C_4H_9$ | $—C_4H_9$ | 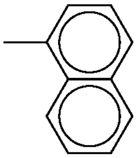 | 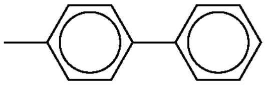 |
| | | | 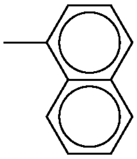 | 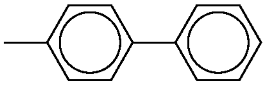 |
| 41 | $—C_4H_8$ | $—C_4H_8$ | 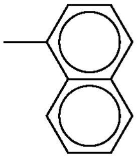 | 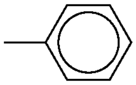 |

-continued
| Compound No. | $R^1$ | $R^2$ | $Ar^1$ / $Ar^3$ | $Ar^2$ / $Ar^4$ |
|---|---|---|---|---|
| | $OCH_3$ | $OCH_3$ | 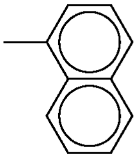 | 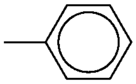 |
| 42 | —$C_8H_{17}$ | —$C_8H_{17}$ | 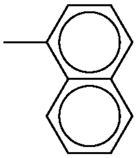 | 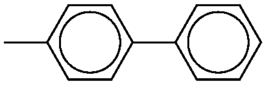 |
| | | | 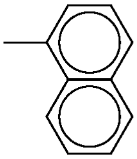 | 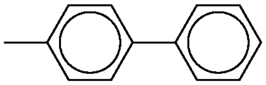 |
| 43 | —$C_8H_{17}$ | —$C_8H_{17}$ | 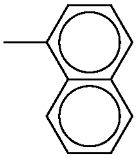 | 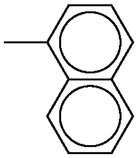 |
| | | | 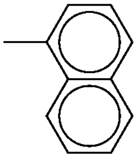 | 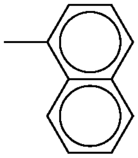 |
| 44 | —$C_8H_{17}$ | —$C_8H_{17}$ | 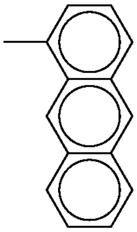 | 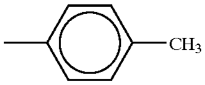 |
| | | | 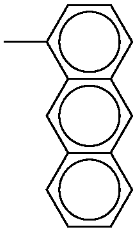 | 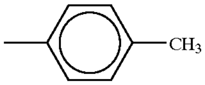 |
| 45 | —$C_{18}H_{37}$ | —$C_{18}H_{37}$ | 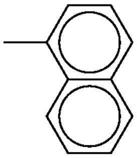 | 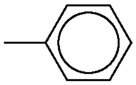 |

-continued
| Compound No. | $R^1$ | $R^2$ | $Ar^1$ $Ar^3$ | $Ar^2$ $Ar^4$ |
|---|---|---|---|---|
| | | | 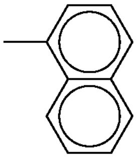 | 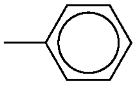 |
Compounds represented by the general formula [2]
| Compound No. | $R^3$ | $R^4$ | $Ar^5$ $Ar^7$ | $Ar^6$ $Ar^8$ |
|---|---|---|---|---|
| 46 | $-C_2H_5$ | $-C_2H_5$ | 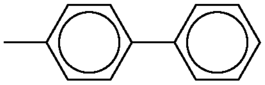 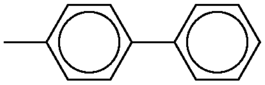 | 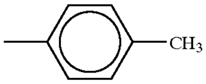 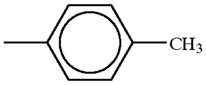 |
| 47 | $-C_2H_5$ | $-C_2H_5$ | 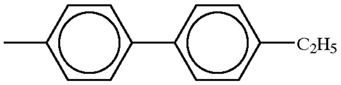 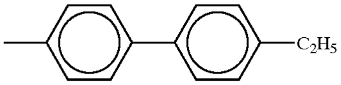 | 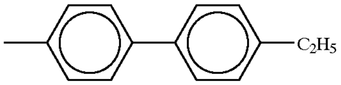 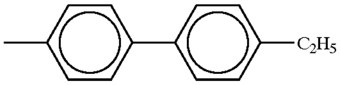 |
| 48 | $-C_2H_5$ | $-C_2H_5$ | 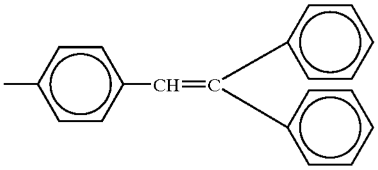 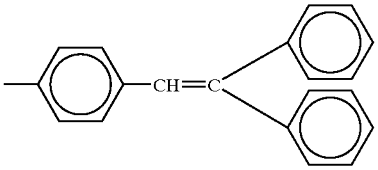 | 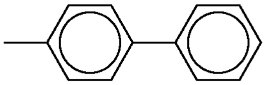 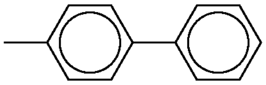 |
| 49 | $-C_2H_5$ | $-C_2H_5$ | 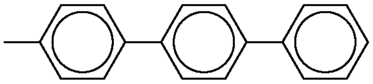 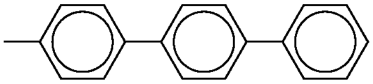 | 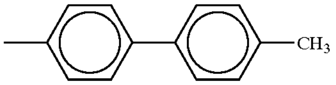 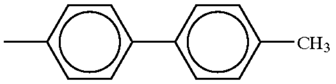 |
| 50 | $-C_2H_5$ | $-C_2H_5$ | 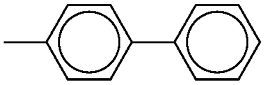 | 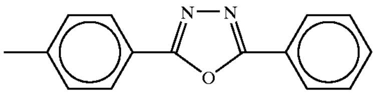 |

-continued
| Compound No. | $R^3$ | $R^4$ | $Ar^5$ $Ar^7$ | $Ar^6$ $Ar^8$ |
|---|---|---|---|---|
| | | | 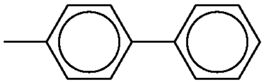 | 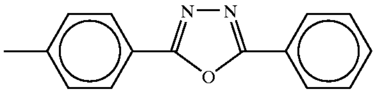 |
| 51 | $-C_3H_7$ | $-C_3H_7$ | 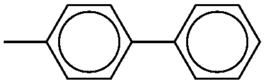 | 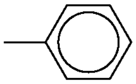 |
| | | | 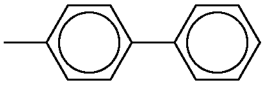 | 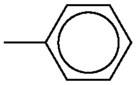 |
| 52 | $-CH_3$ | $-C_3H_7$ | 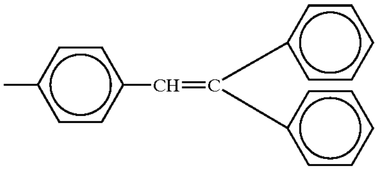 | 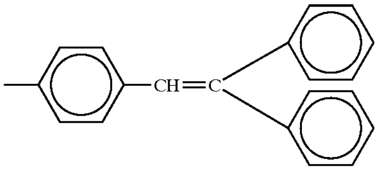 |
| | | | 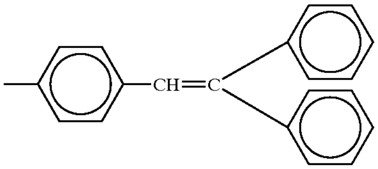 | 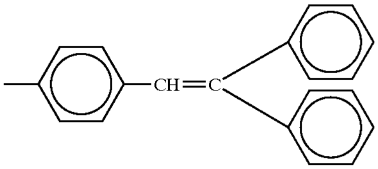 |
| 53 | $-C_3H_7$ | 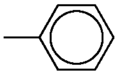 | 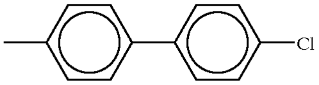 | 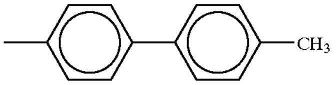 |
| | | | 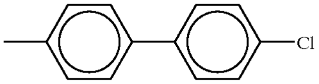 | 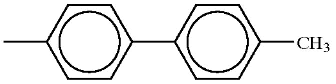 |
| 54 | $-C_4H_9$ | $-C_4H_9$ | 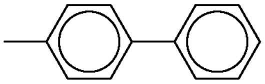 | 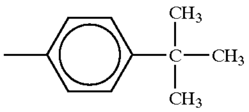 |
| | | | 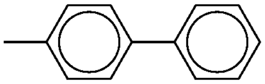 | 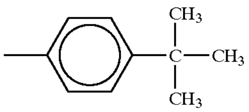 |
| 55 | $-C_4H_9$ | $-C_4H_9$ | 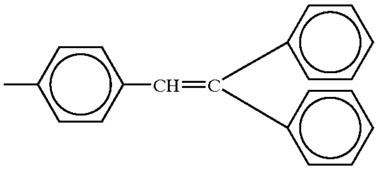 | 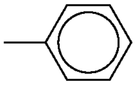 |
| | | | 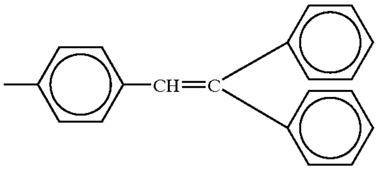 | 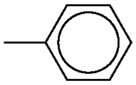 |

-continued
| Compound No. | $R^3$ | $R^4$ | $Ar^5$<br>$Ar^7$ | $Ar^6$<br>$Ar^8$ |
|---|---|---|---|---|
| 56 | 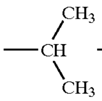 | 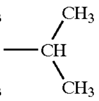 | 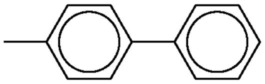 | 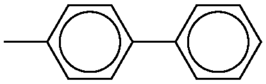 |
| | | | 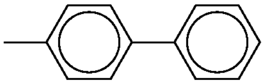 | 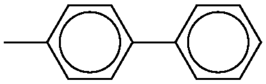 |
| 57 | $-C_8H_{17}$ | $-C_8H_{17}$ | 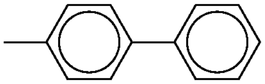 | 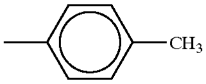 |
| | | | 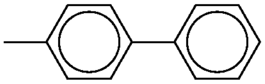 | 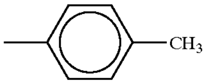 |
| 58 | $-C_8H_{17}$ | $-C_8H_{17}$ | 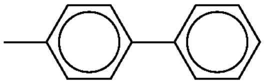 | 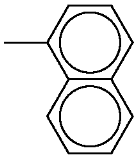 |
| | | | 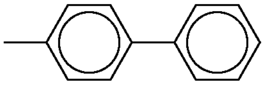 | 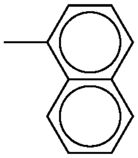 |
| 59 | $-C_8H_{17}$ | $-C_8H_{17}$ | 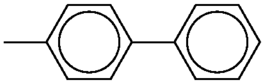 | 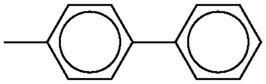 |
| | | | 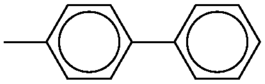 | 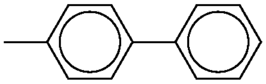 |
| 60 | $-C_{18}H_{37}$ | $-C_{18}H_{37}$ | 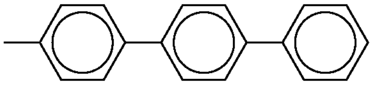 | 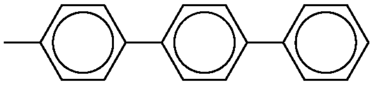 |
| | | | 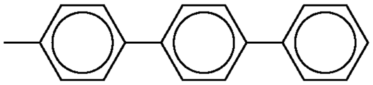 | 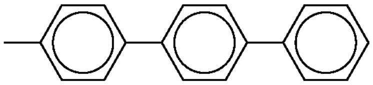 |
| 61 | $-CH_3$ | $-CH_3$ | 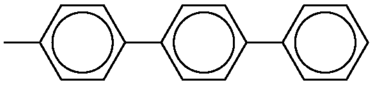 | 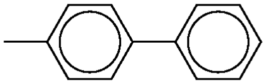 |
| | | | 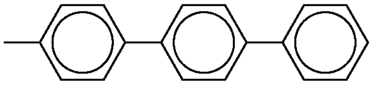 | 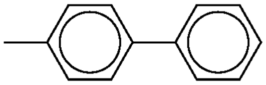 |

-continued
| Compound No. | $R^3$ | $R^4$ | $Ar^5$ / $Ar^7$ | $Ar^6$ / $Ar^8$ |
|---|---|---|---|---|
| 62 | —$CH_3$ | —$CH_3$ | 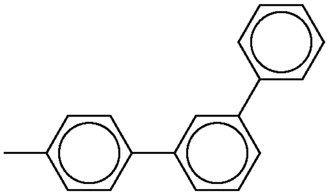 | 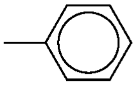 |
| | | | 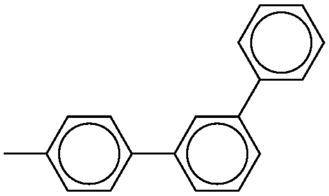 | 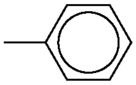 |
| 63 | —$CH_3$ | —$CH_3$ | 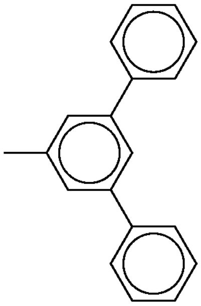 | 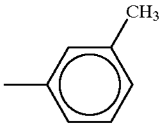 |
| | | | 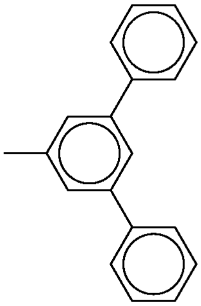 | 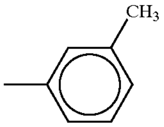 |
| 64 | —$CH_3$ | —$CH_3$ | 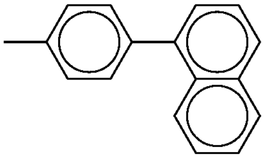 | 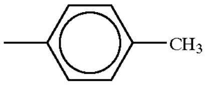 |
| | | | 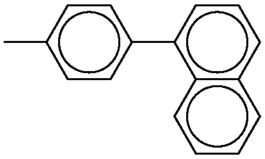 | 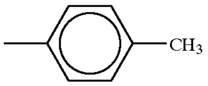 |

-continued
| Compound No. | $R^3$ | $R^4$ | $Ar^5$ / $Ar^7$ | $Ar^6$ / $Ar^8$ |
|---|---|---|---|---|
| 65 | $—CH_3$ | $—CH_3$ | 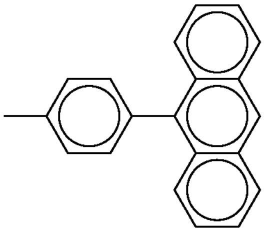 | 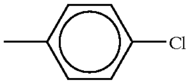 |
| | | | 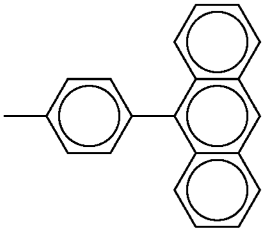 | 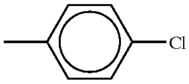 |
| 66 | $—CH_3$ | $—CH_3$ | 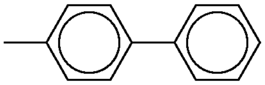 | 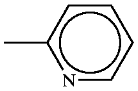 |
| | | | 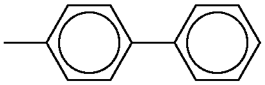 | 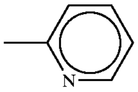 |
| 67 | $—CH_3$ | $—CH_3$ | 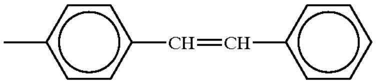 | 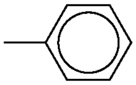 |
| | | | 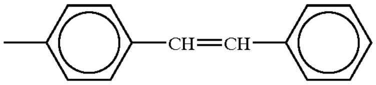 | 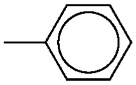 |
| 68 | $—CH_3$ | $—CH_3$ | 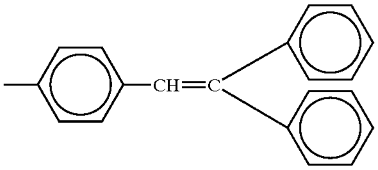 | 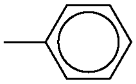 |
| | | | 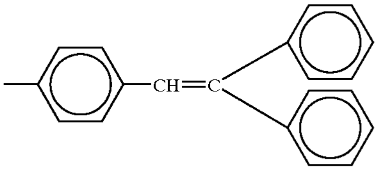 | 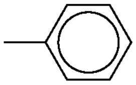 |
| 69 | $—CH_3$ | $—CH_3$ | 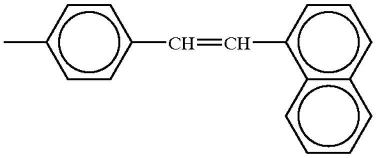 | 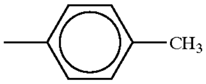 |

-continued
| Compound No. | $R^3$ | $R^4$ | $Ar^5$ $Ar^7$ | $Ar^6$ $Ar^8$ |
|---|---|---|---|---|
| | | | 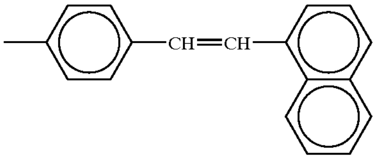 | 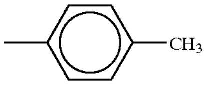 |
| 70 | —$CH_3$ | —$CH_3$ | 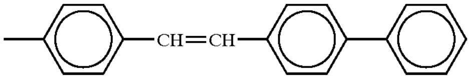 | 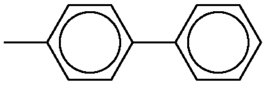 |
| | | | 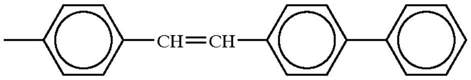 | 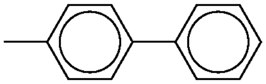 |
| 71 | —$CH_3$ | —$CH_3$ | 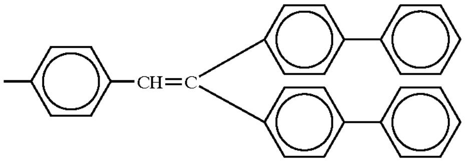 | 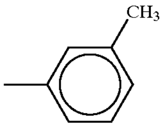 |
| | | | 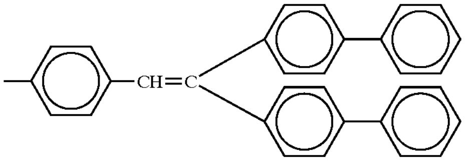 | 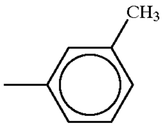 |
| 72 | —$CH_3$ | —$CH_3$ | 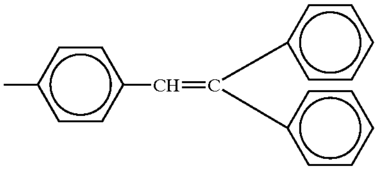 | 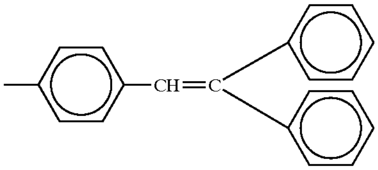 |
| | | | 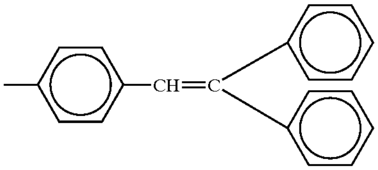 | 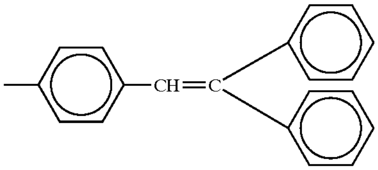 |
| 73 | —$CH_3$ | —$CH_3$ | 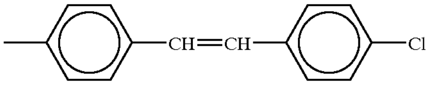 | 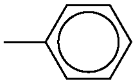 |
| | | | 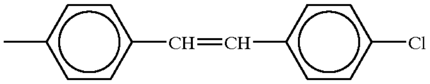 | 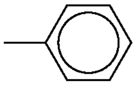 |
| 74 | —$CH_3$ | —$CH_3$ | 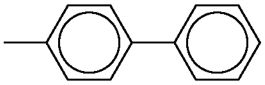 | 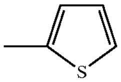 |
| | | | 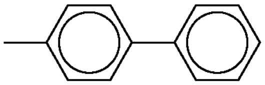 | 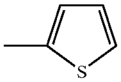 |

-continued
| Compound No. | $R^3$ | $R^4$ | $Ar^5$ $Ar^7$ | $Ar^6$ $Ar^8$ |
|---|---|---|---|---|
| 75 | —$CH_3$ | —$CH_3$ | 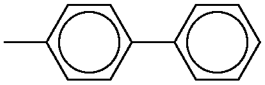 | 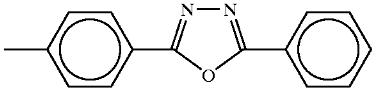 |
| | | | 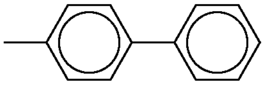 | 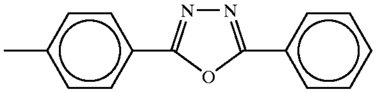 |
| 76 | —H | —H | 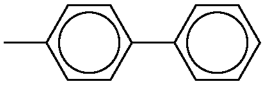 | 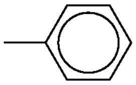 |
| | | | 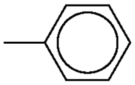 | 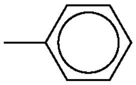 |
| 77 | —H | —H | 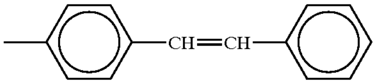 | 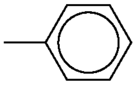 |
| | | | 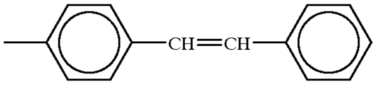 | 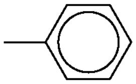 |
| 78 | —H | —H | 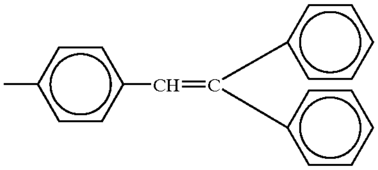 | 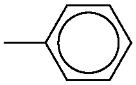 |
| | | | 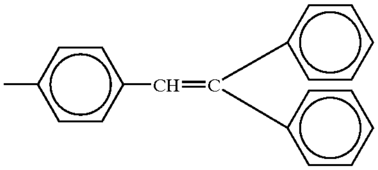 | 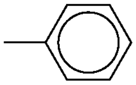 |
| 79 | —H | —H | 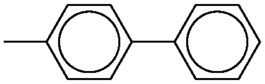 | 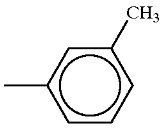 |
| | | | 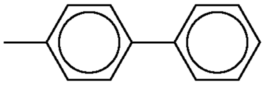 | 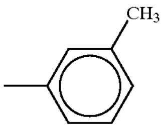 |
| 80 | —H | —H | 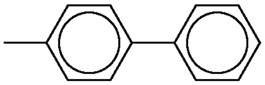 | 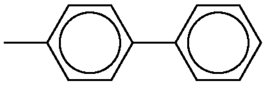 |
| | | | 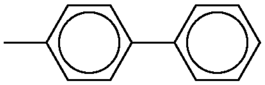 | 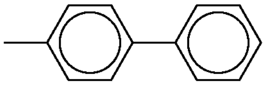 |

-continued
| Compound No. | $R^3$ | $R^4$ | $Ar^5$<br>$Ar^7$ | $Ar^6$<br>$Ar^8$ |
|---|---|---|---|---|
| 81 | —H | —H | 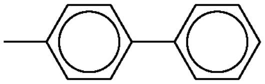 | 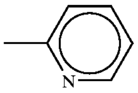 |
| | | | 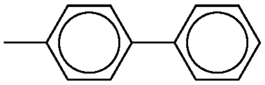 | 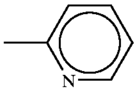 |
| 82 | —H | $—CH_3$ | 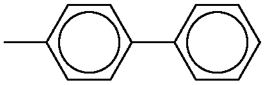 | 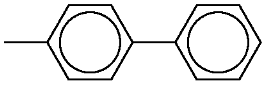 |
| | | | 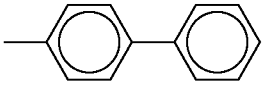 | 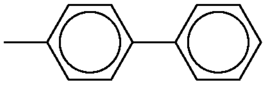 |
| 83 | —H | $—C_3H_7$ | 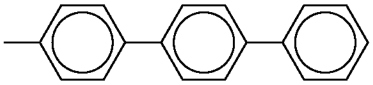 | 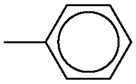 |
| | | | 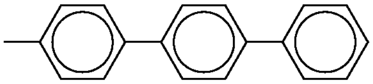 | 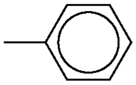 |
| 84 | —H | 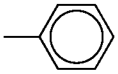 | 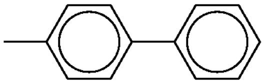 | 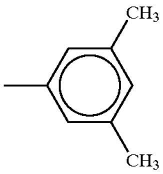 |
| | | | 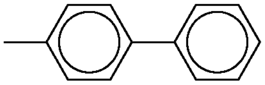 | 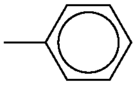 |
| 85 | —H | —Br | 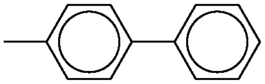 | 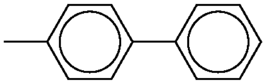 |
| | | | 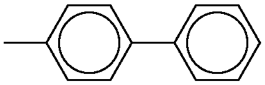 | 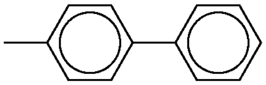 |
| 86 | $—CH_3$ | $—CH_3$ | 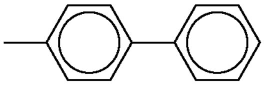 | 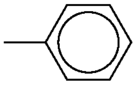 |
| | | | 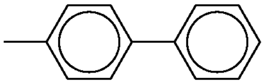 | 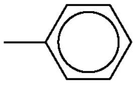 |
| 87 | $—CH_3$ | $—CH_3$ | 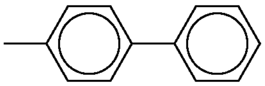 | 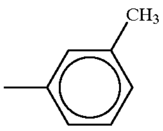 |

-continued

| Compound No. | $R^3$ | $R^4$ | $Ar^5$ $Ar^7$ | $Ar^6$ $Ar^8$ |
|---|---|---|---|---|
| | | | 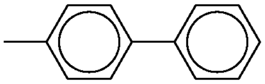 | 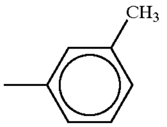 |
| 88 | $—CH_3$ | $—CH_3$ | 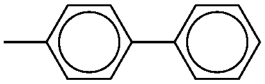 | 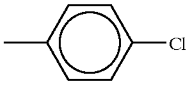 |
| | | | 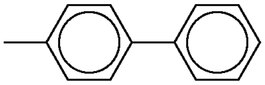 | 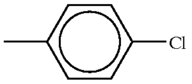 |
| 89 | $—CH_3$ | $—C_3H_7$ | 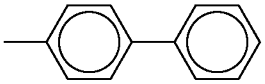 | 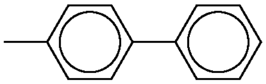 |
| | | | 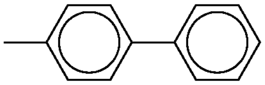 | 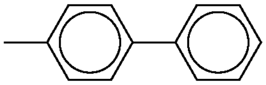 |
| 90 | $—CH_3$ | $—C_3H_7$ | 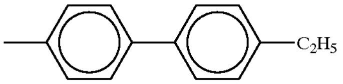 | 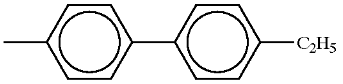 |
| | | | 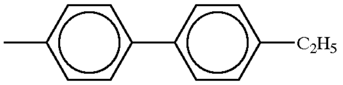 | 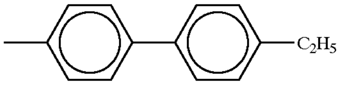 |

The luminescent device in accordance with the present invention has a layer or a plurality of layers composed of an organic compound disposed between an anode and a cathode, and at least one layer among the above organic layers contains a compound represented by the general formula [1] or [2].

The layer of the organic compound represented by the general formula [1] or [2] is formed between the anode and the cathode by a vacuum deposition process or a solution coating process. The thickness of the organic layer is preferably 2 μm or less, and more preferably 0.5 μm or less, and most preferably 0.05 to 0.5 μm.

The present invention will now be described in further detail with reference to the drawings.

FIG. 1 is a schematic cross-sectional view of an embodiment of the luminescent device in accordance with the present invention. An anode 2, a luminescent layer 3 and a cathode 4 are formed on a substrate 1, in that order. In such a configuration, a usable luminescent layer 3 is generally composed of a single compound having hole transportability, electron transportability and luminescence, or a mixture of compounds each having one of these properties.

Figure 2:
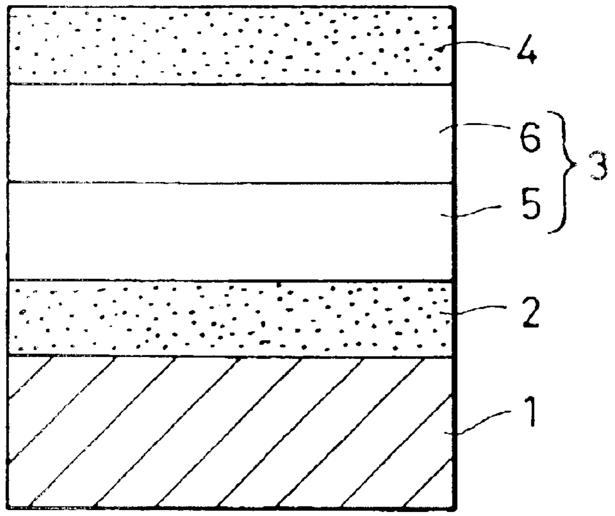
FIG. 2 is a cross-sectional view of another embodiment of a luminescent device in accordance with the present invention.

FIG. 2 is a schematic cross-sectional view of another embodiment of the luminescent device in accordance with the present invention. An anode 2, a hole transport layer 5, an electron transport layer 6 and a cathode 4 are formed on a substrate 1, in that order. The hole transport layer 5 and the electron transport layer 6 function as a luminescent layer 3. In such a configuration, a usable hole transport layer 5 is generally composed of a luminescent material having hole transportability or a mixture including such a material and a non-luminescent material having hole transportability. The luminescent and non-luminescent materials may also have electron transportability. The electron transport layer 6 may be composed of a luminescent material having electron transportability or a mixture including such a material and a non-luminescent material having electron transportability. The luminescent and non-luminescent materials may also have hole transportability.

Figure 3:
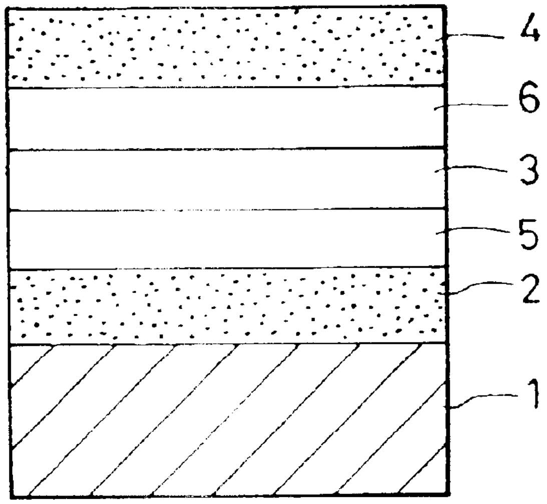
FIG. 3 is a cross-sectional view of a further embodiment of a luminescent device in accordance with the present invention.

FIG. 3 is a schematic cross-sectional view of a further embodiment of the luminescent device in accordance with the present invention. An anode 2, a hole transport layer 5, a luminescent layer 3, an electron transport layer 6 and a cathode 4 are formed on a substrate 1 in that order. In this configuration, carrier transport and luminescence are performed in the individual layers. Such a configuration permits a wide variety of combinations of a material having excellent hole transportability, a material having excellent electron transportability and a material having excellent luminescence. Further, the configuration permits the use of various compounds emitting light at different wavelengths; hence the hue of the luminescent light can be controlled over a wide range. Effective trap of holes and electrons (or excimers) in the central luminescent layer will increase the luminescent efficiency.

Figure 4:
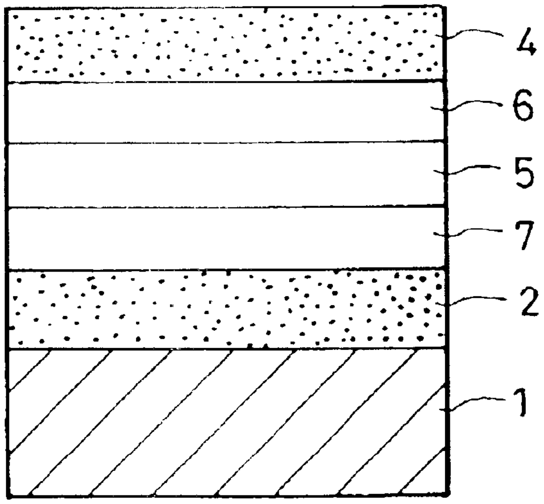
FIG. 4 is a cross-sectional view of a luminescent device in accordance with Example 7 of the present invention.

FIG. 4 is a cross-sectional view of another luminescent device in accordance with the present invention. An anode 2, a hole injection-transport layer 7, a hole transport layer 5, an electron transport layer 6, and a cathode 4 are formed on a substrate 1, in that order. The hole injection-transport layer 7 facilitates hole injection from the anode 2. Thus, the luminescent device can maintain high efficiency for long driving times. In such a configuration, the hole transport layer 5 and/or the electron transport layer 6 function as a luminescent layer.

The compounds represented by the general formulae [1] and [2] have significantly superior luminescent characteristics to conventional compounds and can be used in all the electric field luminescent devices shown in FIGS. 1 to 4.

The compounds represented by the general formulae [1] and [2] have hole transportability and/or electron transportability depending on the structures thereof. In all the embodiments shown in FIGS. 1 to 4, the compounds represented by the general formula [1] may be used alone or in combination, and the compounds represented by the general formula [2] may also be used alone or in combination. Alternatively, the compounds represented by the general formulae [1] and [2] may be used in combination.

As components of the luminescent layer in the luminescent device in accordance with the present invention, hole transport materials studied in the field of electrophotographic photosensitive members and known luminescent hole transport compounds as shown in Tables 1 to 5 or electron transport compounds and known luminescent electron transport materials as shown in Table 6 to 9 can be used with the compounds represented by the general formulae [1] and [2]. These compounds are used alone or in combination.

Table 10 illustrates examples of dopant dyes. The addition of a trace amount of dopant dye in the luminescent layer will significantly increase the luminescent efficiency or will change the luminescent color.

TABLE 1

| Hole Transport Compounds |
| --- |
| 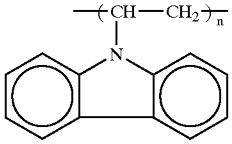 |
| 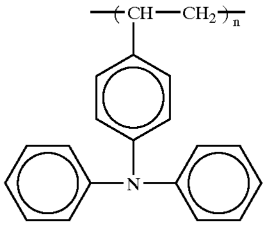 |
| 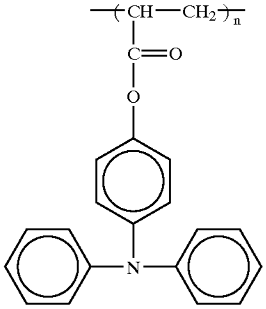 |
| 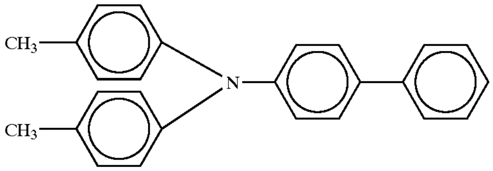 |
| 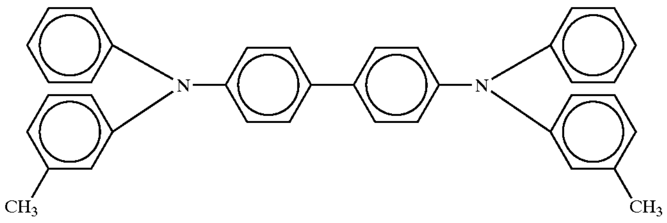 |

TABLE 1-continued
| Hole Transport Compounds |
|---|
| 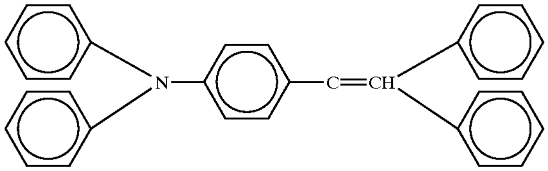 |
TABLE 2
| Hole Transport Compounds |
|---|
| 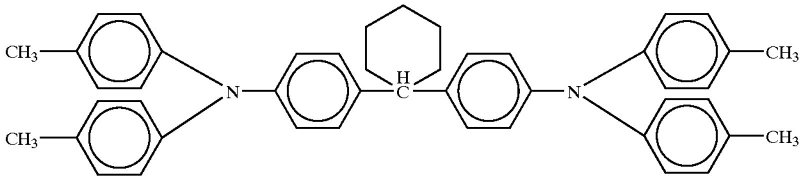 |
| 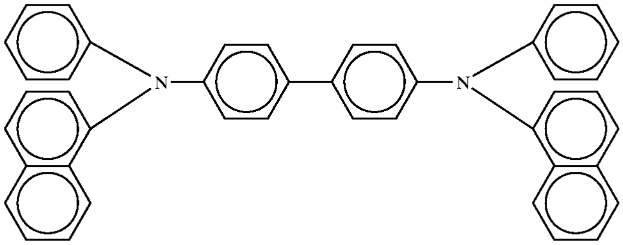 |
| 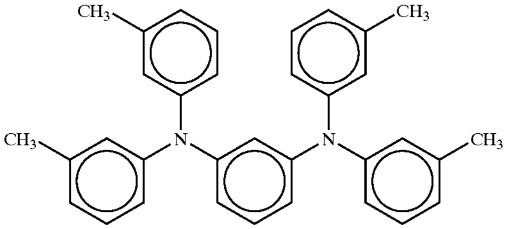 |
| 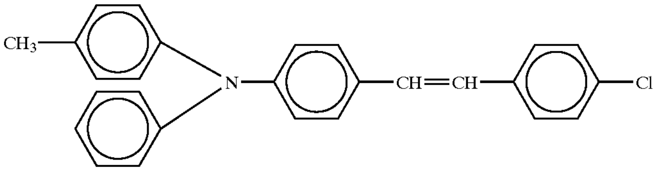 |
| 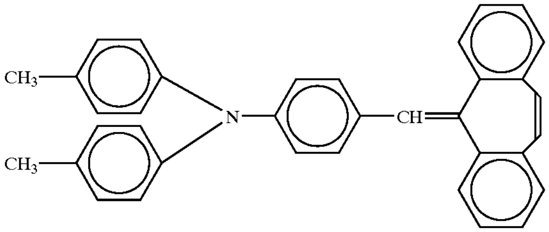 |

TABLE 3
| Hole Transport Compounds |
| --- |
| 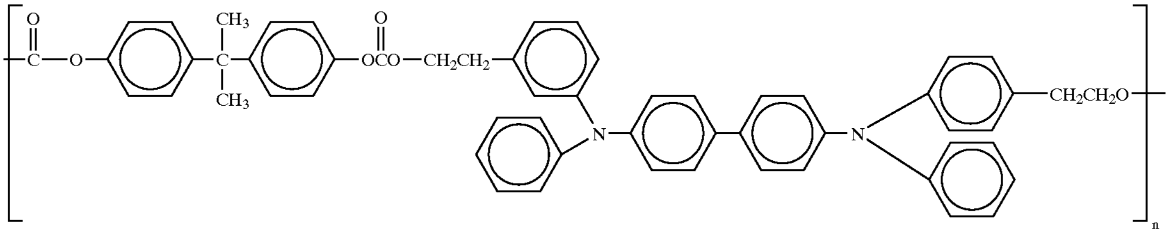 |
TABLE 4
| Hole Transport Compounds |
| --- |
| 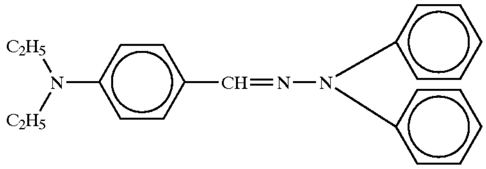 |
| 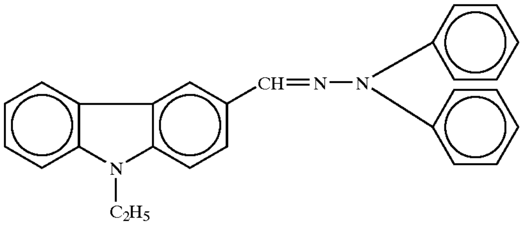 |
| 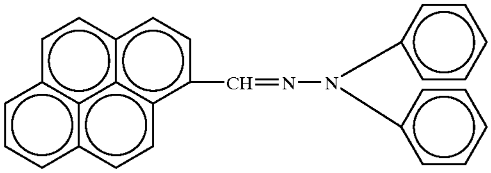 |
| 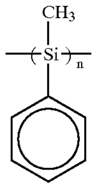 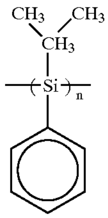 |
TABLE 4-continued
| Hole Transport Compounds |
| --- |
| 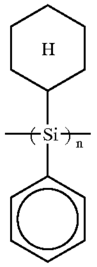 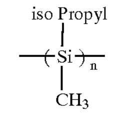 |
TABLE 5
| Hole Transport Compounds |
| --- |
| 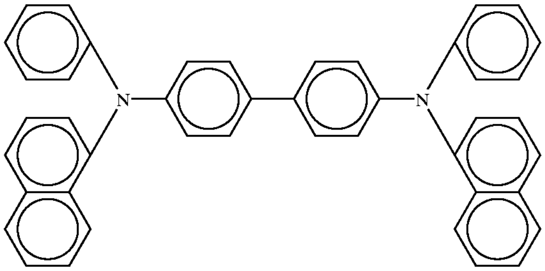 |
| 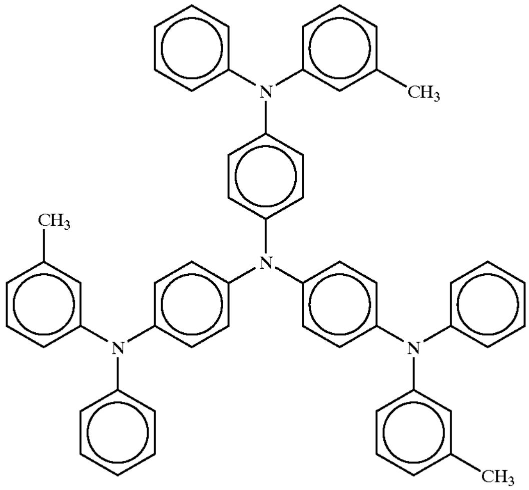 |

TABLE 6
| Electron Transport Compounds | |
|---|---|
| 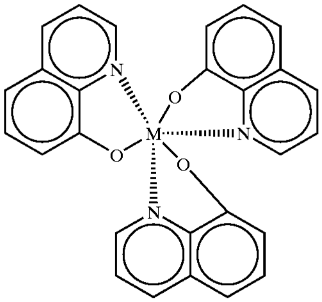 | 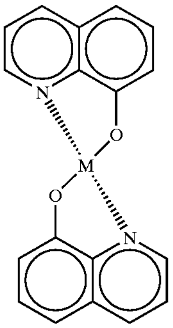 |
| M: Al, Ga | M: Zn, Mg, Be |
| 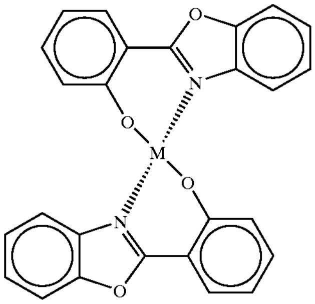 | 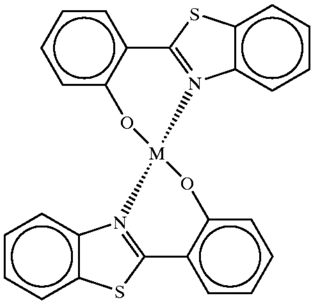 |
| M: Zn, Mg, Be | M: Zn, Mg, Be |
TABLE 7
| Electron Transport Compounds |
|---|
| 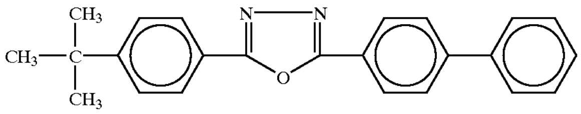 |
| 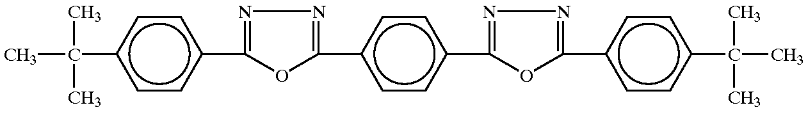 |
| 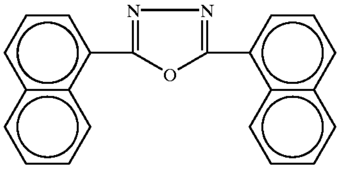 |
| 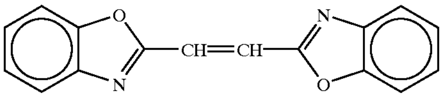 |

TABLE 8
| Electron Transport Compounds |
| --- |
| 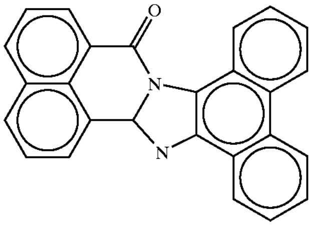 |
| 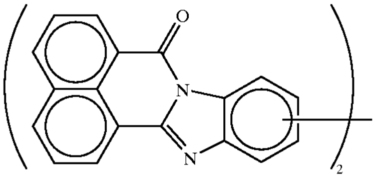 |
| 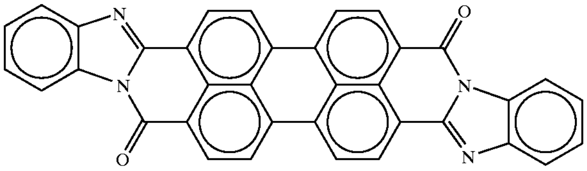 |
| 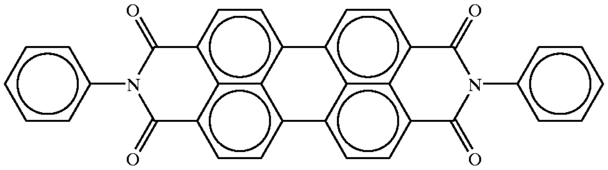 |
TABLE 9
| Electron Transport Compounds |
| --- |
| 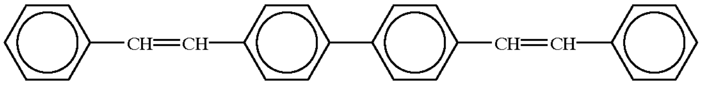 |
| 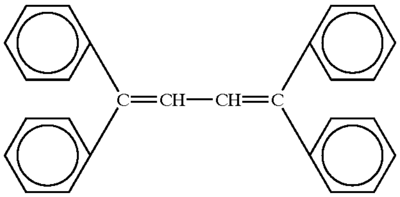 |
| 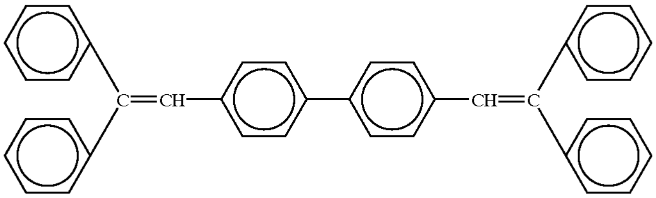 |

TABLE 9-continued
| Electron Transport Compounds |
|---|
| 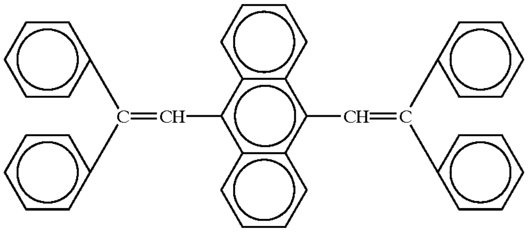 |
| 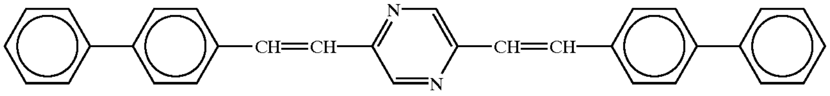 |
| 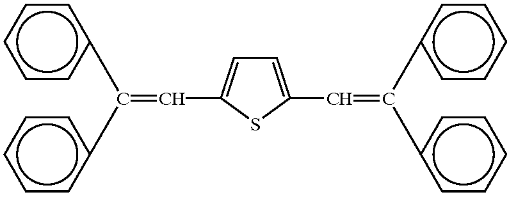 |
TABLE 10
| Dopant Dyes | |
|---|---|
| 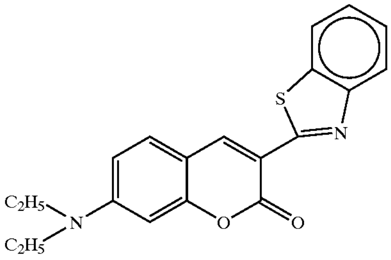 | 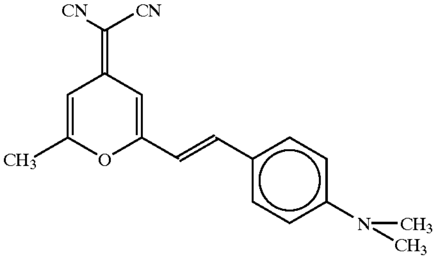 |
| 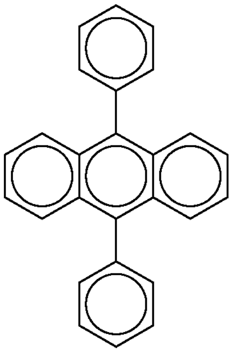 | 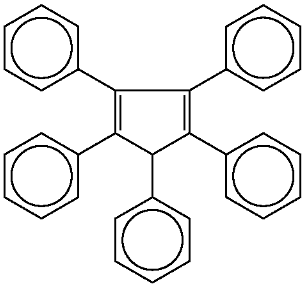 |

TABLE 10-continued

| Dopant Dyes | |
|---|---|
| 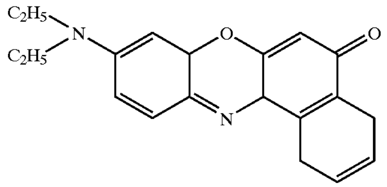 | 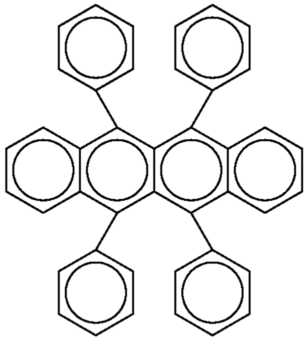 |
| 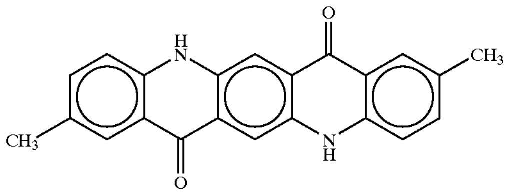 | |

In the luminescent device in accordance with the present invention, the luminescent layer containing the compounds represented by the general formulae [1] and [2] and the other organic layer are generally formed by a vacuum deposition process or using a binding resin.

Non-limiting examples of the binding resins include polyvinyl carbazole resins, polycarbonate resins, polyester resins, polyarylate resins, butyral resins, polystyrene resins, polyvinyl acetal resins, diallyl phthalate resins, acrylic resins, methacrylic resins, phenol resins, epoxy resins, silicon resins, polysulfone resins, and urea resins. These binding resins can be used alone or in combination.

Preferable anode materials have large work functions. Examples of such materials include nickel, gold, platinum, palladium, selenium, rhenium, and iridium; alloys thereof; and tin oxide, indium tin oxide, and copper iodide. Conductive polymers, such as poly(3-methylthiophene), polyphenylene sulfide and polypyrrole are also usable.

In contrast, preferable cathode materials have small work functions. Examples of such materials include silver, lead, tin, magnesium, aluminum, calcium, manganese, indium and chromium, and alloys thereof.

It is preferable that at least one electrode of the anode and cathode transmits 50% or more of incident light over the wavelength region of the luminescent light.

As the transparent substrate, glass and plastic films are used in the present invention.

EXAMPLES

The present invention is described in further detail with reference to the following examples.

Synthesis of N,N,N',N'-tetra-(1-naphthyl)-2,7-diamino-9,9-dimethylfluorene (Compound 13)

Into a 100-ml egg-plant type flask, 2.24 g (10 mmol) of 2,7-diamino-9,9-dimethylfluorene, 15.22 g (160 mmol) of 1-iodonaphthalene, 6.91 g(50 mmol) of potassium carbonate, 12.71 g (200 mmol) of powdered copper, and 50 ml of o-dichlorobenzene were fed, and the mixture was refluxed with stirring for 24 hours.

The reactant solution was cooled and then filtered, and the filtrate was concentrated under reduced pressure. Into the concentrated solution, 35 ml of acetone was added and then filtered to collect precipitated crude crystal. The crude crystal was purified through a silica gel column using a toluene-hexane mixture, and 6.13 g (yield: 84.1%) of pale yellow fine crystal N,N,N',N'-tetra-(1-naphthyl)-2,7-diamino-9,9-dimethylfluorene (Compound 13) was prepared.

Figure 5:
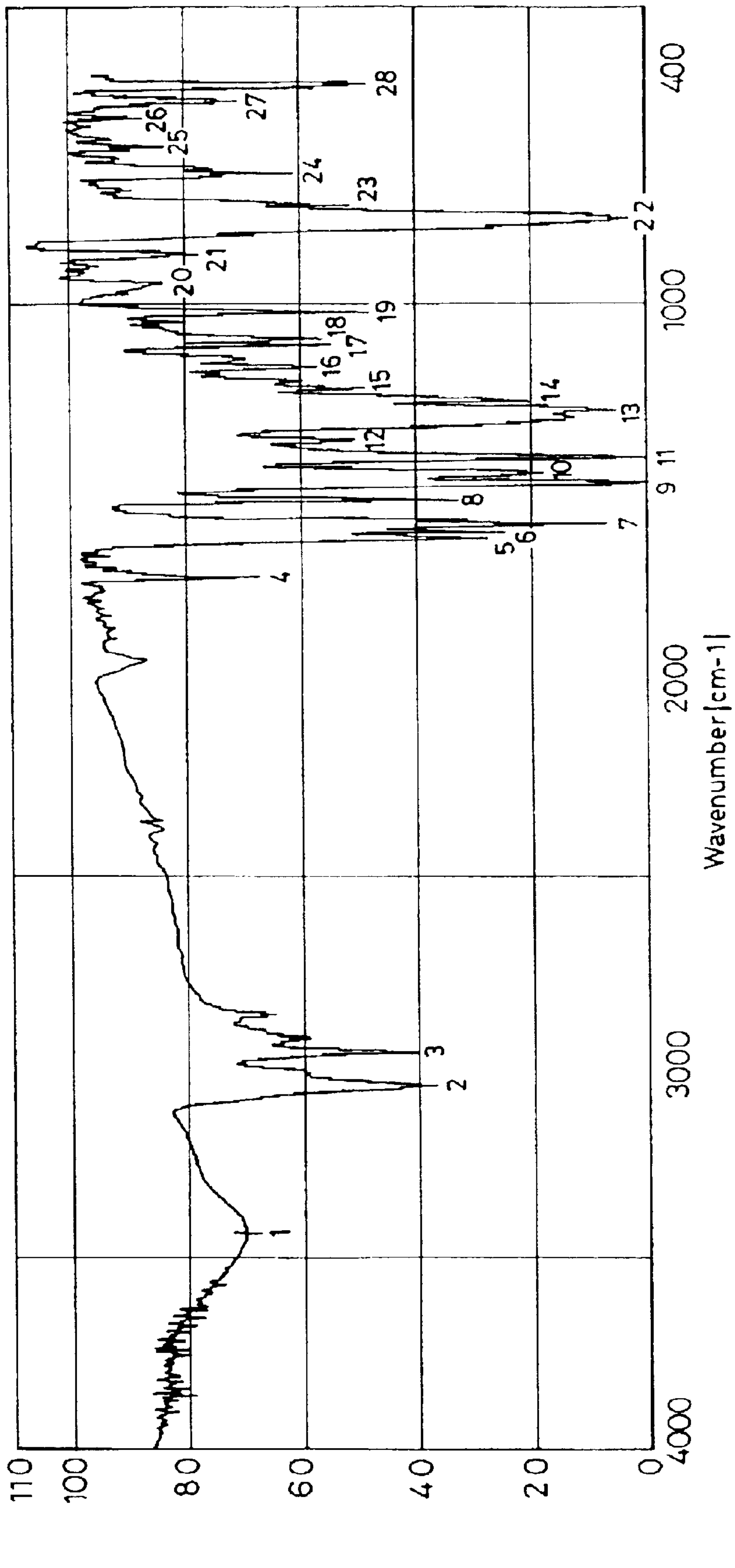
FIG. 5 is an infrared spectrum of an organic compound in accordance with the present invention.

The melting point (Tm) and the glass transition temperature (Tg) of the resulting compound were 331.0 to 332.7° C. and 169° C., respectively, according to differential scanning calorimetry using Pyris 1 by Perkin Elmer Corporation. FIG. 5 is an IR spectrum of the compound by a KBr tablet method using an FT-IR spectrophotometer (FT-IR-420) by JASCO.

Example 1

An indium tin oxide (ITO) film with a thickness of 100 nm was formed on a glass substrate by a sputtering process. After the transparent substrate was cleaned, a layer of Compound 12 with a thickness of 65 nm was deposited thereon at a deposition rate of 0.2 to 0.3 nm/sec. Then, a 65 nm thick aluminum quinolinol film was formed. Thereafter, a Mg—Ag metallic electrode having an atomic ratio of Mg:Ag=10:1 was formed by a vacuum deposition process at a deposition rate of 2.0 nm/sec under a vacuum pressure of 3 to $4\times10^{-6}$ torr. A luminescent device was thereby formed.

A direct current of 10 V was applied between the ITO anode and the Mg—Ag cathode of the luminescent device. A current flow of 175 $mA/cm^2$ and a green luminescence with a luminance of 5,300 $cd/m^2$ were observed. A voltage with a current density of 3.0 $mA/cm^2$ was applied to the sample for 100 hours. The luminance was 160 $cd/m^2$ at the start and changed to 140 $cd/m^2$ at the end.

Examples 2 to 6

Luminescent devices were prepared as in EXAMPLE 1 using Compounds 21, 36, 47, 72 and 88 instead of Compound 12. Table 11 shows the characteristics of these luminescent devices.

TABLE 11

| | | Initial | | After 100 hours | |
|---|---|---|---|---|---|
| EXAMPLE | Compound | Applied Voltage (V) | Luminance ($cd/m^2$) | Applied Voltage (V) | Luminance ($cd/m^2$) |
| 2 | 21 | 5.3 | 350 | 5.9 | 345 |
| 3 | 36 | 6.7 | 275 | 7.8 | 280 |
| 4 | 47 | 4.8 | 345 | 5.7 | 330 |
| 5 | 72 | 4.9 | 550 | 5.5 | 530 |
| 6 | 88 | 5.7 | 450 | 3.8 | 450 |

Comparative Example 1

A luminescent device was prepared as in EXAMPLE 1 using the following compound instead of Compound 12.

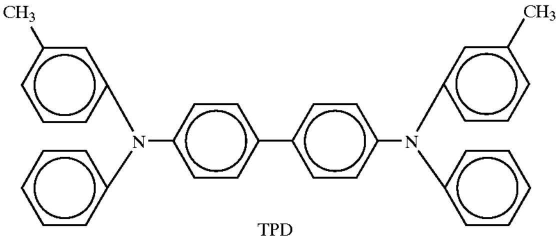

TPD

A direct current of 15 V was applied between the ITO anode and the Mg—Ag cathode of the luminescent device. A current flow of 15 $mA/cm^2$ and a green luminescence with a luminance of 35 $cd/m^2$ were observed. A voltage with a current density of 27 $mA/cm^2$ was applied to the sample for 100 hours. The luminance was 100 $cd/m^2$ at the start and decreased to 8 $cd/m^2$ at the end.

The results of EXAMPLES 1 to 6 and COMPARATIVE EXAMPLE 1 show that the compounds in accordance with the present invention have high luminance and prolonged life compared to the comparative amine compound.

Example 7

A luminescent device shown in FIG. 4 was prepared as follows. An indium tin oxide (ITO) anode 2 with a thickness of 100 nm was formed on a glass substrate by a sputtering process. After the transparent substrate was cleaned, a m-MTDATA hole injection-transport layer 7 with a thickness of 20 nm was formed thereon, and a layer of Compound 32 with a thickness of 50 nm was deposited thereon as a hole transport layer 5. Furthermore, an electron transport layer of an electron transport compound ($Alq_3$) with a thickness of 65 nm was formed thereon, and then an aluminum cathode 4 with a thickness of 140 nm was formed thereon.

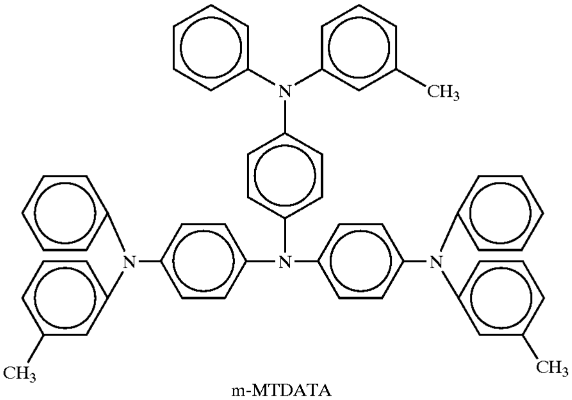

m-MTDATA

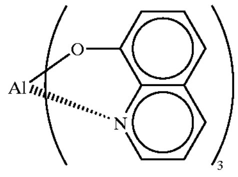

$Alq_3$

A direct current of 5 V was applied between the ITO anode and the aluminum cathode of the luminescent device. A current flow of 10 $mA/cm^2$ and a green luminescence with a luminance of 576 $cd/m^2$ were observed. A voltage with a current density of 3.0 $mA/cm^2$ was applied to the sample for 100 hours. The luminance was 265 $cd/m^2$ at the start and slightly changed to 250 $cd/m^2$ at the end.

As described above, luminescent devices using compounds represented by the general formulae [1] and [2] in accordance with the present invention have significantly high luminance for a low applied-voltage, and high durability. A large device can be readily formed by a vacuum deposition process or a casting process with relatively low production costs.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A luminescent device comprising a pair of electrodes and a luminescent layer disposed therebetween, wherein the luminescent layer comprises a compound of formula (12):

(12)

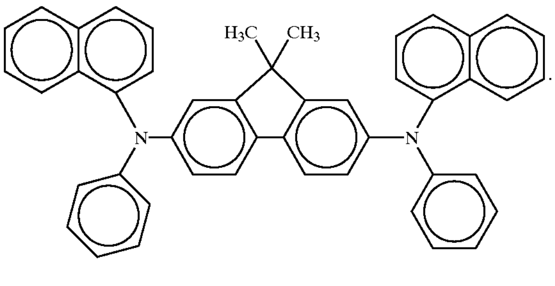

2. A luminescent device comprising a pair of electrodes and a luminescent layer disposed therebetween, wherein the luminescent layer comprises a compound of formula (13):

(13)

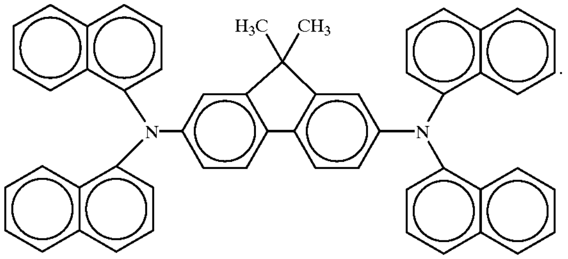

3. A luminescent device comprising a pair of electrodes and a luminescent layer disposed therebetween, the luminescent layer comprises a compound represented by the following general formula (1) and a compound represented by the following general formula (2):

(1)

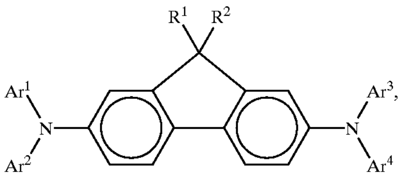

wherein $R^1$ and $R^2$ are each independently a hydrogen atom, a halogen atom, substituted or unsubstituted alkyl group, a substituted or unsubstituted alkoxy group, or a substituted or unsubstituted aryl group; $Ar^1$, $Ar^2$, $Ar^3$, and $Ar^4$ are each a substituted or unsubstituted aryl or heterocyclic group, which may be the same or different from each other; both $Ar^1$ and $Ar^3$ are fused aromatic rings; and at least one of $R^1$ and $R^2$ is a hydrogen, a halogen, a substituted or unsubstituted alkyl group, or a substituted or unsubstituted alkoxy group; and (2)

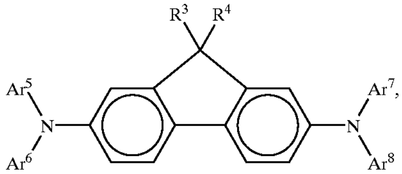

wherein $R^3$ and $R^4$ are each independently a hydrogen atom, a halogen atom, a substituted or unsubstituted alkyl group, a substituted or unsubstituted alkoxy group, or a substituted or unsubstituted aryl group; $Ar^5$, $Ar^6$, $Ar^7$, and $Ar^8$ are each a substituted or unsubstituted aryl or heterocyclic group, which may be the same or different from each other; at least one of $Ar^5$, $Ar^6$, $Ar^7$, and $Ar^8$ is a π-conjugated aromatic hydrocarbon having 12 or more carbon atoms selected from the group consisting of a polyphenyl and a stilbene; and at least one of $R^3$ and $R^4$ is a halogen, a substituted or unsubstituted alkyl group, or a substituted or unsubstituted alkoxy group.

* * * * *